(12) United States Patent
Dunkel et al.

(10) Patent No.: US 7,897,780 B2
(45) Date of Patent: Mar. 1, 2011

(54) METHOD FOR CONTROLLING PHYTOPATHOGENIC FUNGI USING SILYLATED CARBOXAMIDES

(75) Inventors: Ralf Dunkel, Lyons (FR); Hans-Ludwig Elbe, Wuppertal (DE); Benoit Hartmann, Langenfeld (DE); Jörg Nico Greul, Leichlingen (DE); Alexander Klausener, Pulheim (DE); Stefan Herrmann, Langenfeld (DE); Ronald Ebbert, Nürnberg (DE); Peter Dahmen, Neuss (DE); Karl-Heinz Kuck, Langenfeld (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 36 days.

(21) Appl. No.: 10/592,685

(22) PCT Filed: Mar. 4, 2005

(86) PCT No.: PCT/EP2005/002284
§ 371 (c)(1), (2), (4) Date: Aug. 27, 2007

(87) PCT Pub. No.: WO2005/095392
PCT Pub. Date: Oct. 13, 2005

(65) Prior Publication Data
US 2007/0293455 A1 Dec. 20, 2007

(30) Foreign Application Priority Data
Mar. 17, 2004 (DE) .......................... 10 2004 012 901

(51) Int. Cl.
A01N 55/10 (2006.01)
C07D 277/30 (2006.01)
(52) U.S. Cl. ......................................... 548/110; 514/63
(58) Field of Classification Search .................. None
See application file for complete search history.

(56) References Cited

U.S. PATENT DOCUMENTS

| | | | |
|---|---|---|---|
| 5,223,526 A | 6/1993 | McLoughlin et al. | |
| 5,330,995 A | 7/1994 | Eicken et al. | |
| 5,416,103 A | 5/1995 | Eicken et al. | |
| 5,438,070 A | 8/1995 | Eicken et al. | |
| 5,486,621 A | 1/1996 | Phillion et al. | |
| 5,922,732 A | 7/1999 | Urch et al. | |
| 7,582,589 B2 * | 9/2009 | Ehrenfreund et al. | 504/280 |
| 2001/0046975 A1 | 11/2001 | Phillion et al. | |
| 2002/0061913 A1 | 5/2002 | Urch et al. | |
| 2002/0119982 A1 | 8/2002 | Wang et al. | |
| 2004/0204470 A1 | 10/2004 | Elbe et al. | |
| 2005/0182107 A1 | 8/2005 | Ehrenfreund et al. | |
| 2006/0154967 A1 | 7/2006 | Ehrenfreund et al. | |
| 2006/0276434 A1 * | 12/2006 | Ehrenfreund et al. | 514/63 |
| 2007/0191454 A1 | 8/2007 | Dunkel et al. | |

FOREIGN PATENT DOCUMENTS

| | | |
|---|---|---|
| DE | 103 25 439 A1 | 12/2004 |
| EP | 0 538 231 A1 | 4/1993 |
| EP | 0 545 099 A2 | 6/1993 |
| EP | 0 589 301 A1 | 3/1994 |
| EP | 0 589 313 A1 | 3/1994 |
| WO | WO 93/11117 A1 | 6/1993 |
| WO | WO 96/37494 A1 | 11/1996 |
| WO | WO 98/25923 A1 | 6/1998 |
| WO | WO 03/010149 A1 | 2/2003 |
| WO | WO 03/080628 A1 | 10/2003 |
| WO | WO 2004/099195 A1 | 11/2004 |

OTHER PUBLICATIONS

Danielli et al., ARKIVOC, 2000, 1(1), pp. 58-62.*
Lukevics, E., "Biological Activity of Nitrogen-Containing Organosilicon Compounds," *Nobel Symp.*, No. 40:435-445, Almqvist & Wiksell (1978).
Database CAPLUS, Chemical Abstracts Service, Accession No. 1984:5549, Hellwinkel, D., et al., 1 page (1984).
Database CAPLUS, Chemical Abstracts Service, Accession No. 1988:75166, Sakamoto, T., et al., 1 page (1988).
Database CAPLUS, Chemical Abstracts Service, Accession No. 1990:423608, Bartoli, G., 1 page (1990).
Database CAPLUS, Chemical Abstracts Service, Accession No. 2004:189014, Costa, M., et al., 2 pages (Apr. 2004).
International Search Report for International Application No. PCT/EP2004/012590, mailed Feb. 18, 2005, European Patent Office, Netherlands.
Dialog File 351, Accession No. 6970179, WPI English language abstract for EP 0 589 301 (Listed on accompanying PTO/SB/08A as document FP6).
Dialog File 351, Accession No. 6720672, WPI English language abstract for EP 0 589 313 (Listed on accompanying PTO/SB/08A as document FP7).
Dialog File 351, Accession No. 14683529, WPI English language abstract for DE 103 25 439 (Listed on accompanying PTO/SB/08A as document FP11).
Co-pending U.S. Appl. No. 11/629,982, inventors Kneen, G., et al., filed Dec. 19, 2006 (Not Published).
Co-pending U.S. Appl. No. 10/597,723, inventors Dunkel, R., et al., filed May 16, 2007 (Not Published).

(Continued)

*Primary Examiner* — Laura L. Stockton
(74) *Attorney, Agent, or Firm* — Sterne, Kessler, Goldstein & Fox P.L.L.C.

(57) ABSTRACT

Novel silylated carboxamides of the formula (I)

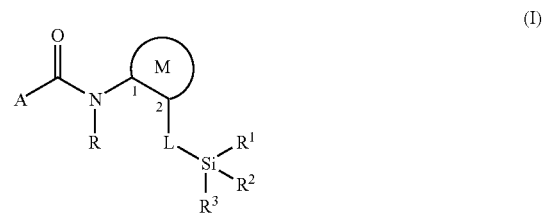

(I)

in which M, L, $R^1$, $R^2$, $R^3$, R and A are as defined in the description,
a plurality of processes for preparing these compounds and their use for controlling unwanted microorganisms, and also novel intermediates and their preparation.

4 Claims, No Drawings

OTHER PUBLICATIONS

Co-pending U.S. Appl. No. 11/817,373, inventor Straub, A., filed Aug. 29, 2007 (Not Published).

Abbiati, G., et al., "An Efficient Synthesis of 2,4-Substituted [1,8]Naphthyridines from 3-(2-Amino-5-methylpyridin-3-yl)-1-arylprop-2-yn-1-ones," *Synthesis* 13:1912-1916, Georg Thieme Verlag Stuttgart (2002).

Jóźwiak, A., et al., "Behaviour of *N*-Pyridylbenzamides versus Benzanilides in the *ortho*-Directed Lithiation of Masked Aromatic Carboxylic Acids," *Eur. J. Org. Chem.* 2004:3254-3261, Wiley-VCH Verlag GmbH & Co. KGaA (2004).

Sakamoto, T., et al., "Condensed Heteroaromatic Ring Systems. XII. Synthesis of Indole Derivatives from Ethyl 2-Bromocarbanilates," *Chem. Pharm. Bull.* 35:1823-1828, Pharmaceutical Society of Japan (1987).

Venuti, M.C., et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," *J. Med. Chem.* 31:2136-2145, American Chemical Society (1988).

Xu, L., et al., "Transition Metal Catalyzed Synthesis of 5-Azaindoles," *Tetrahedron Lett.* 39:5159-5162, Elsevier Science Ltd. (1998).

International Search Report for International Appplication No. PCT/EP2005/002284, European Patent Office, Netherlands, mailed on Aug. 2, 2005.

\* cited by examiner

METHOD FOR CONTROLLING PHYTOPATHOGENIC FUNGI USING SILYLATED CARBOXAMIDES

The present invention relates to novel silylated carboxamides, to a plurality of processes for their preparation and to their use for controlling unwanted microorganisms.

It is already known that numerous carboxamides have fungicidal properties (cf., for ex-ample, WO 03/080628, WO 03/010149, EP-A 0 589 301, EP-A 0 545 099). The activity of these compounds is good; however, it is sometimes, for example at low application rates, unsatisfactory. Silylated carboxamides having a heterocycle as amide component have hitherto not been disclosed.

This invention now provides novel silylated carboximides of the formula (I)

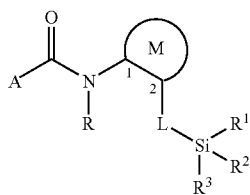

in which
M represents a thiophine, pyridine, pyrimidine, pyridazine or pyrazine ring, each of which is monosubstituted by $Y^1$, or represents a thiazole ring substituted by $Y^2$, $Y^1$ represents hydrogen, fluorine, chlorine, bromine, methyl, isopropyl, methylthio or trifluoromethyl, $Y^2$ represents hydrogen, fluorine, chlorine, bromine, methyl, methylthio or trifluoromethyl, L represents a direct bond or represents straight-chain or branched alkylene (alkanediyl), alkenylene (alkenediyl) or alkynylene (alkynediyl), each of which is optionally substituted, $R^1$ and $R^2$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, $R^3$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_{2-6}$-haloalkenyl, $C_2$-$C_6$-haloalkynyl, $C_3$-$C_6$-cycloalkyl, or represent in each case optionally substituted phenyl or phenylalkyl, R represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-$C_1$-$C_3$-alkyl)carbonyl-$C_1$-$C_3$-alkyl, halo-$C_1$-$C_3$-alkoxycarbonyl-$C_1$-$C_3$-alkyl having in each case 1 to 13 fluorine, chlorine and/or bromine atoms;
($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$, $R^4$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^5$ and $R^6$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^5$ and $R^6$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^9$, $R^7$ and $R^8$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^7$ and $R^8$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^9$, $R^9$ represents hydrogen or $C_1$-$C_6$-alkyl, A represents the radical of the formula (A1)

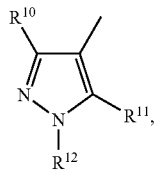

in which
$R^{10}$ represents hydrogen, hydroxyl, formyl, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, $R^{11}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkylthio having in each case 1 to 5 halogen atoms, and $R^{12}$ represents hydrogen, $C_1$-$C_4$-alkyl, hydroxy-$C_1$-$C_4$-alkyl, $C_2$-$C_6$-alkenyl, $C_3$-$C_6$-cyclo-alkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or represents phenyl, or
A represents the radical of the formula (A2)

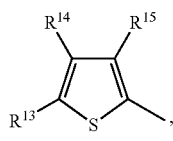

in which
$R^{13}$ and $R^{14}$ independently of one another represent hydrogen, halogen, $C_1$-$C_4$-alkyl or $C_1$-$C_4$-haloalkyl having 1 to 5 halogen atoms and $R^{15}$ represents halogen, cyano or $C_1$-$C_4$-alkyl, or $C_1$-$C_4$-haloalkyl or $C_1$-$C_4$-haloalkoxy having in each case 1 to 5 halogen atoms, or A represents the radical of the formula (A3)

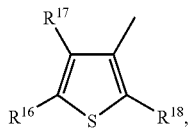
(A3)

in which
  $R^{16}$ and $R^{17}$ independently of one another represent hydrogen, halogen, $C_1$-$C_4$-alkyl or $C_1$-$C_4$-haloalkyl having 1 to 5 halogen atoms and
  $R^{18}$ represents hydrogen, $C_1$-$C_4$-alkyl or $C_1$-$C_4$-haloalkyl having 1 to 5 halogen atoms, or A represents the radical of the formula (A4)

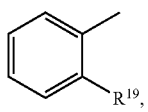
(A4)

in which
  $R^{19}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, or A represents the radical of the formula (A5)

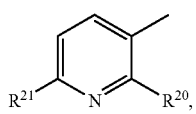
(A5)

in which
  $R^{20}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms and
  $R^{21}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, or A represents the radical of the formula (A6)

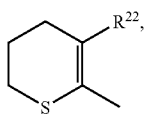
(A6)

in which
  $R^{22}$ represents $C_1$-$C_4$-alkyl or $C_1$-$C_4$-haloalkyl having 1 to 5 halogen atoms, or A represents the radical of the formula (A7)

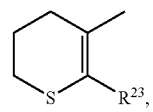
(A7)

in which
  $R^{23}$ represents $C_1$-$C_4$-alkyl or $C_1$-$C_4$-haloalkyl having 1 to 5 halogen atoms, or A represents the radical of the formula (A8)

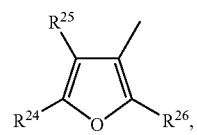
(A8)

in which
  $R^{24}$ and $R^{25}$ independently of one another represent hydrogen, halogen, amino, $C_1$-$C_4$-alkyl or $C_1$-$C_4$-haloalkyl having 1 to 5 halogen atoms and
  $R^{26}$ represents hydrogen, $C_1$-$C_4$-alkyl or $C_1$-$C_4$-haloalkyl having 1 to 5 halogen atoms, or A represents the radical of the formula (A9)

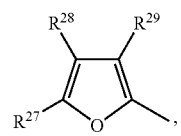
(A9)

in which
  $R^{27}$ and $R^{28}$ independently of one another represent hydrogen, halogen, amino, nitro, $C_1$-$C_4$-alkyl or $C_1$-$C_4$-haloalkyl having 1 to 5 halogen atoms and
  $R^{29}$ represents halogen, $C_1$-$C_4$-alkyl or $C_1$-$C_4$-haloalkyl having 1 to 5 halogen atoms, or A represents the radical of the formula (A10)

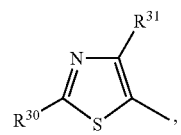
(A10)

in which
  $R^{30}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms and
  $R^{31}$ represents halogen, hydroxyl, $C_1$-$C_4$-alkyl, $C_1$-$C_4$-alkoxy, $C_3$-$C_6$-cycloalkyl, $C_1$-$C_4$-haloalkyl or $C_1$-$C_4$-haloalkoxy having in each case 1 to 5 halogen atoms, or
A represents the radical of the formula (A11)

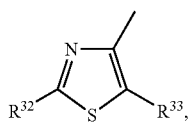
(A11)

in which
R$^{32}$ represents hydrogen, halogen, amino, C$_1$-C$_4$-alkylamino, di(C$_1$-C$_4$-alkyl)amino, cyano, C$_1$-C$_4$-alkyl or C$_1$-C$_4$-haloalkyl having 1 to 5 halogen atoms and
R$^{33}$ represents halogen, C$_1$-C$_4$-alkyl or C$_1$-C$_4$-haloalkyl having 1 to 5 halogen atoms,
or
A represents the radical of the formula (A12)

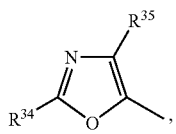
(A12)

in which
R$^{34}$ represents hydrogen or C$_1$-C$_4$-alkyl and
R$^{35}$ represents halogen, C$_1$-C$_4$-alkyl or C$_1$-C$_4$-haloalkyl having 1 to 5 halogen atoms,
or
A represents the radical of the formula (A13)

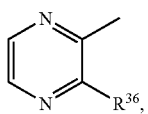
(A13)

in which
R$^{36}$ represents hydrogen, halogen, C$_1$-C$_4$-alkyl or C$_1$-C$_4$-haloalkyl having 1 to 5 halogen atoms,
or
A represents the radical of the formula (A14)

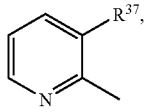
(A14)

in which
R$^{37}$ represents halogen, hydroxyl, C$_1$-C$_4$-alkyl, C$_1$-C$_4$-alkoxy, C$_1$-C$_4$-alkylthio, C$_1$-C$_4$-haloalkyl, C$_1$-C$_4$-haloalkylthio or C$_1$-C$_4$-haloalkoxy having in each case 1 to 5 halogen atoms,
or
A represents the radical of the formula (A15)

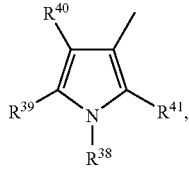
(A15)

in which
R$^{38}$ represents hydrogen, cyano, C$_1$-C$_4$-alkyl, C$_1$-C$_4$-haloalkyl having 1 to 5 halogen atoms, C$_1$-C$_4$-alkoxy-C$_1$-C$_4$-alkyl, hydroxy-C$_1$-C$_4$-alkyl, C$_1$-C$_4$-alkylsulphonyl di(C$_1$-C$_4$-alkyl)aminosulphonyl, C$_1$-C$_6$-alkylcarbonyl or represents in each case optionally substituted phenylsulphonyl or benzoyl,
R$^{39}$ represents hydrogen, halogen, C$_1$-C$_4$-alkyl or C$_1$-C$_4$-haloalkyl having 1 to 5 halogen atoms,
R$^{40}$ represents hydrogen, halogen, cyano, C$_1$-C$_4$-alkyl or C$_1$-C$_4$-haloalkyl having 1 to 5 halogen atoms,
R$^{41}$ represents hydrogen, halogen, C$_1$-C$_4$-alkyl or C$_1$-C$_4$-haloalkyl having 1 to 5 halogen atoms,
or
A represents the radical of the formula (A16)

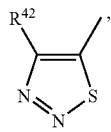
(A16)

in which
R$^{42}$ represents halogen, C$_1$-C$_4$-alkyl or C$_1$-C$_4$-haloalkyl having 1 to 5 halogen atoms,
or
A represents the radical of the formula (A17)

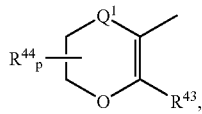
(A17)

in which
R$^{43}$ represents C$_1$-C$_4$-alkyl or C$_1$-C$_4$-haloalkyl having 1 to 5 halogen atoms,
R$^{44}$ represents C$_1$-C$_4$-alkyl,
Q$^1$ represents S (sulphur), O (oxygen), SO, SO$_2$ or CH$_2$,
p represents 0, 1 or 2, where the radicals R$^{44}$ are identical or different if p is 2.

The compounds according to the invention can, if appropriate, be present as mixtures of various possible isomeric forms, in particular of stereoisomers, such as, for example, E and Z, threo and erythro, and also optical isomers, and, if appropriate, also of tautomers. What is claimed are both the E and the Z isomers, and also the threo and erythro and the optical isomers, any mixtures of these isomers and the possible tautomeric forms.

Furthermore, it has been found that silylated carboxamides of the formula (I) are obtained when
a) carboxylic acid derivatives of the formula (II)

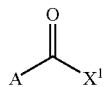
(II)

in which
A is as defined above and
X$^1$ represents halogen or hydroxyl,
are reacted with an amine of the formula (III)

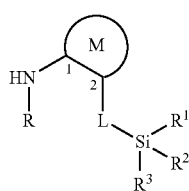
(III)

in which M, L, R$^1$, R$^2$, R$^3$ and R are as defined above,
if appropriate in the presence of a catalyst, if appropriate in the presence of a condensing agent, if appropriate in the presence of an acid binder and if appropriate in the presence of a diluent, or b) silylated carboxamides of the formula (I-a)

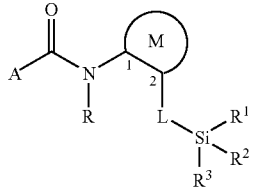
(I-a)

in which M, L, A, $R^1$, $R^2$ and $R^3$ are as defined above
are reacted with halides of the formula (IV)

$$R^4\text{---}X^2 \quad (IV)$$

in which $X^2$ represents chlorine, bromine or iodine, $R^4$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl) carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$, where $R^4$, $R^5$, $R^6$, $R^7$ and $R^8$ are as defined above, in the presence of a base and in the presence of a diluent.

Finally, it has been found that the novel silylated carboxamides of the formula (I) have very good microbicidal properties and can be used for controlling unwanted microorganisms both in crop protection and in the protection of materials.

The formula (I) provides a general definition of the silylated carboxamides according to the invention. Preferred radical definitions of the formulae shown above and below are given below. These definitions apply both to the end products of the formula (I) and likewise to all intermediates.

M preferably represents one of the heterocycles below

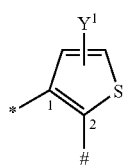
M-1

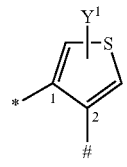
M-2

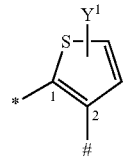
M-3

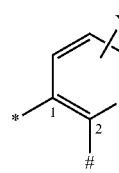
M-4

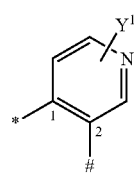
M-5

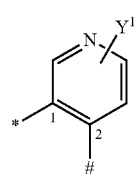
M-6

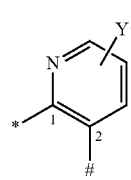
M-7

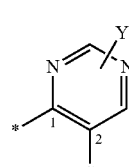
M-8

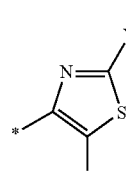
M-9

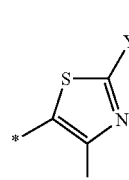
M-10

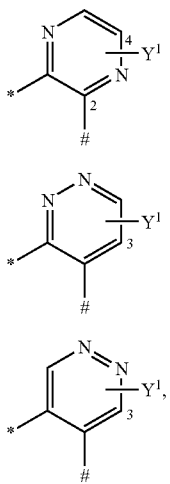

where the bond marked "*" is attached to the amide and the bond marked "#" is attached to the radical L.

M particularly preferably represents a heterocycle selected from the group consisting of M-1, M-2, M-3, M-4, M-5, M-7, M-8, M-9 and M-10.

M very particularly preferably represents a heterocycle selected from the group consisting of M-1, M-4, M-5, M-7, M-8, M-9 and M-10.

M especially preferably represents the heterocycle M-1.

M furthermore especially preferably represents the heterocycle M4.

M furthermore especially preferably represents the heterocycle M-5.

M furthermore especially preferably represents the heterocycle M-7.

M furthermore especially preferably represents the heterocycle M-8.

M furthermore especially preferably represents the heterocycle M-9.

M furthermore especially preferably represents the heterocycle M-10.

$Y^1$ preferably represents hydrogen.

$Y^1$ furthermore, if M represents M-1, M-2 or M-3, preferably represents chlorine, where chlorine is particularly preferably located in the 5-position (M-1, M-2) or in the 3-position (M-3).

$Y^1$ furthermore, if M represents M-1, M-2 or M-3, preferably represents fluorine, where fluorine is particularly preferably located in the 5-position (M-1, M-2) or in the 3-position (M-3).

$Y^1$ furthermore, if M represents M-1, M-2 or M-3, preferably represents methyl, where methyl is particularly preferably located in the 5-position (M-1, M-2) or in the 3-position (M-3).

$Y^1$ furthermore, if M represents M-4, M-5, M-6 or M-7, preferably represents fluorine, where fluorine is particularly preferably located in the 6-position (M-4, M-5) or in the 3-position (M-6, M-7) steht.

$Y^1$ furthermore, if M represents M-4, M-5, M-6 or M-7, preferably represents chlorine, where chlorine is particularly preferably located in the 6-position (M-4, M-5) or in the 3-position (M-6, M-7) steht.

$Y^1$ furthermore, if M represents M-4, M-5, M-6 or M-7, preferably represents methyl, where methyl is particularly preferably located in the 4-position (M4) or in the 3-position (M-5, M-6, M-7).

$Y^1$ furthermore, if M represents M-8, preferably represents methyl, where methyl is particularly preferably located in the 3-position.

$Y^1$ furthermore, if M represents M-8, preferably represents trifluoromethyl, where trifluoromethyl is particularly preferably located in the 3-position.

$Y^1$ furthermore, if M represents M-11, preferably represents methyl, where methyl is particularly preferably located in the 4-position.

$Y^1$ furthermore, if M represents M-11, preferably represents trifluoromethyl, where trifluoromethyl is particularly preferably located in the 4-position.

$Y^1$ furthermore, if M represents M-12, preferably represents methyl, where methyl is particularly preferably located in the 3-position.

$Y^1$ furthermore, if M represents M-12, preferably represents trifluoromethyl, where trifluoromethyl is particularly preferably located in the 3-position.

$Y^1$ furthermore, if M represents M-13, preferably represents methyl, where methyl is particularly preferably located in the 3-position.

$Y^1$ furthermore, if M represents M-13, preferably represents trifluoromethyl, where trifluoro-1-methyl is particularly preferably located in the 3-position.

$Y^2$ preferably represents hydrogen.

$Y^2$ preferably represents fluorine.

$Y^2$ preferably represents chlorine.

$Y^2$ furthermore preferably represents methyl.

$Y^2$ furthermore preferably represents trifluoromethyl.

L preferably represents a direct bond or represents optionally halogen-substituted straight-chain or branched $C_1$-$C_6$-alkylene, $C_2$-$C_6$-alkenylene or $C_2$-$C_6$-alkynylene.

L particularly preferably represents a direct bond or represents —$CH_2$—, —$(CH_2)_2$—, —$(CH_2)_3$—, —CH(Me)-, —CH(Me)$CH_2$—, —$CH_2$CH(Me)-, —CH(Me)CH(Me)-, —C($Me_2$)$CH_2$—, —CH(Me)-$(CH_2)_2$—, —CH(Me)-$(CH_2)_3$—, —CH═CH—, —C(Me)═CH— or —C≡C—.

L very particularly preferably represents —$(CH_2)_2$—, —$(CH_2)_3$—, —CH(Me)-, —CH(Me)$CH_2$—, —CH(Me)-$(CH_2)_2$—, —CH(Me)-$(CH_2)_3$—, —CH═CH—, —C(Me)═CH— or —C≡C—.

$R^1$ and $R^2$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^1$ and $R^2$ independently of one another particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^1$ and $R^2$ independently of one another very particularly preferably represent methyl, methoxy, methoxymethyl or methylthiomethyl.

$R^1$ and $R^2$ especially preferably each represent methyl.

$R^3$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^3$ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^3$ very particularly preferably represents methyl, ethyl, n- or isopropyl, iso- or tert-butyl, methoxy, isopropoxy, iso- or tert-butoxy, methoxymethyl, methylthiomethyl or phenyl.

$R^3$ especially preferably represents methyl, ethyl, n- or isopropyl, iso- or tert-butyl, methoxy, isopropoxy, iso- or tert-butoxy.

$R^3$ most preferably represents methyl.

R preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-$C_1$-$C_3$-alkyl)carbonyl-$C_1$-$C_3$-alkyl, halo-($C_{1-3}$-alkoxy)carbonyl-$C_1$-$C_3$-alkyl having in each case 1 to 13 fluorine, chlorine and/or bromine atoms; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$.

R particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^4$, —CONR$^5$R$^6$ or —CH$_2$NR$^7$R$^8$.

R very particularly preferably represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —(CH$_2$—O—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^4$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^4$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^5$ and $R^6$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^5$ and $R^6$ furthermore together with the nitrogen atom to which they are attached preferably form a saturated heterocycle having 5 or 6 ring atoms which is optionally mono- to tetrasubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^9$.

$R^5$ and $R^6$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluormethoxymethyl.

$R^5$ and $R^6$ furthermore together with the nitrogen atom to which they are attached particularly preferably represent a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^9$.

$R^7$ and $R^8$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^7$ and $R^8$ furthermore together with the nitrogen atom to which they are attached preferably represent a saturated heterocycle having 5 or 6 ring atoms which is optionally mono- to tetrasubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^9$.

$R^7$ and $R^8$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^7$ and $R^8$ furthermore together with the nitrogen atom to which they are attached particularly preferably represent a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by $R^9$.

$R^9$ preferably represents hydrogen or $C_1$-$C_4$-alkyl.

$R^9$ particularly preferably represents hydrogen, methyl, ethyl, n- or isopropyl, n-, iso-, sec- or tert-butyl.

A preferably represents one of the radicals
A1, A2, A3, A4, A5, A8, A9, A10, A11, A12, A13, A14, A15 or A17 indicated above.

A particularly preferably represents one of the radicals
A1, A2, A4, A5, A8, A10, A11, A12, A13, A14, A15 or A17 indicated above.

A very particularly preferably represents the radical A1.

A furthermore very particularly preferably represents the radical A2.

A furthermore very particularly preferably represents the radical A4.

A furthermore very particularly preferably represents the radical A5.
A furthermore very particularly preferably represents the radical A8.
A furthermore very particularly preferably represents the radical A10.
A furthermore very particularly preferably represents the radical A11.
A furthermore very particularly preferably represents the radical A12.
A furthermore very particularly preferably represents the radical A13.
A furthermore very particularly preferably represents the radical A14.
A furthermore very particularly preferably represents the radical A15.
A furthermore very particularly preferably represents the radical A17.

$R^{10}$ preferably represents hydrogen, hydroxyl, formyl, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

$R^{10}$ particularly preferably represents hydrogen, hydroxyl, formyl, fluorine, chlorine, bromine, iodine, methyl, ethyl, isopropyl, methoxy, ethoxy, monofluoromethyl, monofluoroethyl, difluoromethyl, trifluoromethyl, difluorochloromethyl, trichloromethyl, dichloromethyl, pentafluoroethyl, cyclopropyl, methoxy, ethoxy, trifluoromethoxy, difluoromethoxy, trichloromethoxy, methylthio, ethylthio, trifluoromethylthio or difluoromethylthio.

$R^{10}$ very particularly preferably represents hydrogen, hydroxyl, formyl, fluorine, chlorine, bromine, iodine, methyl, ethyl, isopropyl, methoxy, cyclopropyl, monofluoromethyl, monofluoroethyl, difluoromethyl, dichloromethyl, trifluoromethyl, difluorochloromethyl, trichloromethyl, —CHFCH$_3$ or difluoromethoxy.

$R^{10}$ especially preferably represents hydrogen, hydroxyl, formyl, chlorine, methyl, ethyl, methoxy, cyclopropyl, monofluoromethyl, difluoromethyl, dichloromethyl, trifluoromethyl, —CHFCH$_3$ or difluoromethoxy.

$R^{11}$ preferably represents hydrogen, fluorine, chlorine, bromine, iodine, methyl, ethyl, methoxy, ethoxy, methylthio, ethylthio, $C_1$-$C_2$-haloalkyl having 1 to 5 fluorine, chlorine and/or bromine atoms, $R^{11}$ particularly preferably represents hydrogen, fluorine, chlorine, bromine, iodine, methyl or —CHFCH$_3$.

$R^{12}$ very particularly preferably represents hydrogen, fluorine, chlorine or methyl.

$R^{12}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{12}$ particularly preferably represents hydrogen, methyl, ethyl, isopropyl, trifluoromethyl, difluoromethyl, hydroxymethyl, hydroxyethyl or phenyl.

$R^{12}$ very particularly preferably represents hydrogen, methyl, trifluoromethyl or phenyl.

$R^{12}$ especially preferably represents methyl.

$R^{13}$ and $R^{14}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{13}$ and $R^{14}$ independently of one another particularly preferably represents hydrogen, fluorine, chlorine, bromine, methyl, ethyl, difluoromethyl, trifluoromethyl, difluorochloromethyl or trichloromethyl.

$R^{13}$ and $R^{14}$ independently of one another very particularly preferably represent hydrogen, fluorine, chlorine, bromine, methyl, ethyl, difluoromethyl, trifluoromethyl or trichloromethyl.

$R^{13}$ and $R^{14}$ especially preferably each represent hydrogen.

$R^{15}$ preferably represents fluorine, chlorine, bromine, iodine, cyano, methyl, ethyl, $C_1$-$C_2$-haloalkyl or $C_1$-$C_2$-haloalkoxy having in each case 1 to 5 fluorine, chlorine and/or bromine atoms.

$R^{15}$ particularly preferably represents fluorine, chlorine, bromine, iodine, cyano, methyl, trifluoromethyl, trifluoromethoxy, difluoromethoxy, difluorochloromethoxy or trichloromethoxy.

$R^{15}$ very particularly preferably represents fluorine, chlorine, bromine, iodine, methyl, trifluoromethyl or trifluoromethoxy.

$R^{15}$ especially preferably represents chlorine, bromine, iodine, trifluoromethyl or methyl.

$R^{16}$ and $R^{17}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{16}$ and $R^{17}$ independently of one another particularly preferably represent hydrogen, fluorine, chlorine, bromine, methyl, ethyl, difluoromethyl, trifluoromethyl, difluorochloromethyl or trichloromethyl.

$R^{16}$ and $R^{17}$ independently of one another very particularly preferably represent hydrogen, fluorine, chlorine, bromine or methyl.

$R^{16}$ and $R^{17}$ especially preferably each represent hydrogen.

$R^{18}$ preferably represents hydrogen, methyl, ethyl or $C_1$-$C_2$-haloalkyl having 1 to 5 fluorine, chlorine and/or bromine atoms.

$R^{18}$ particularly preferably represents hydrogen, methyl or trifluoromethyl.

$R^{18}$ very particularly preferably represents methyl.

$R^{19}$ preferably represents hydrogen, fluorine, chlorine, bromine, iodine, hydroxyl, cyano, $C_1$-$C_4$-alkyl, $C_1$-$C_2$-haloalkyl, $C_{1-2}$-haloalkoxy or $C_1$-$C_2$-haloalkylthio having in each case 1 to 5 fluorine, chlorine and/or bromine atoms.

$R^{19}$ particularly preferably represents hydrogen, fluorine, chlorine, bromine, iodine, hydroxyl, cyano, methyl, ethyl, n-propyl, isopropyl, n-butyl, iso-butyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{19}$ very particularly preferably represents hydrogen, fluorine, chlorine, bromine, iodine, methyl, difluoromethyl, trifluoromethyl or trichloromethyl.

$R^{19}$ especially preferably represents bromine, iodine, methyl, difluoromethyl or trifluoromethyl.

$R^{20}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{20}$ particularly preferably represents fluorine, chlorine, bromine, iodine, hydroxyl, cyano, methyl, ethyl, n-propyl, isopropyl, n-butyl, iso-butyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{20}$ very particularly preferably represents fluorine, chlorine, bromine, iodine, methyl, trifluoromethyl, difluoromethyl or trichloromethyl.

$R^{21}$ preferably represents hydrogen, fluorine, chlorine, bromine, iodine, cyano, C1-C4-alkyl, methoxy, ethoxy, methylthio, ethylthio, C1-C2-haloalkyl or C1-C2-haloalkoxy having in each case 1 to 5 fluorine, chlorine and/or bromine atoms, $C_1$-$C_2$-alkylsulphinyl or C1-C2-alkylsulphonyl.

$R^{21}$ particularly preferably represents hydrogen, fluorine, chlorine, bromine, iodine, cyano, n-propyl, isopropyl, n-butyl, iso-butyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{21}$ very particularly preferably represents hydrogen, fluorine, chlorine, bromine, iodine, n-propyl, isopropyl, n-butyl, iso-butyl, sec-butyl, tert-butyl, trifluoromethyl, difluoromethyl, trichloromethyl, methylsulphinyl or methylsulphonyl.

$R^{21}$ especially preferably represents hydrogen.

$R^{22}$ preferably represents methyl, ethyl or $C_{1-2}$-haloalkyl having 1 to 5 fluorine, chlorine and/or bromine atoms.

$R^{22}$ particularly preferably represents methyl, ethyl, trifluoromethyl, difluoromethyl, difluorochloromethyl or trichloromethyl.

$R^{22}$ very particularly preferably represents methyl, trifluoromethyl, difluoromethyl or trichloromethyl.

$R^{23}$ preferably represents methyl, ethyl or $C_1$-$C_2$-haloalkyl having 1 to 5 fluorine, chlorine and/or bromine atoms.

$R^{23}$ particularly preferably represents methyl, ethyl, trifluoromethyl, difluoromethyl, difluorochloromethyl or trichloromethyl.

$R^3$ very particularly preferably represents methyl, trifluoromethyl, difluoromethyl or trichloromethyl.

$R^{24}$ and $R^{25}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{24}$ and $R^{25}$ independently of one another particularly preferably represent hydrogen, fluorine, chlorine, bromine, methyl, ethyl, trifluoromethyl, difluoromethyl, difluorochloromethyl or trichloromethyl.

$R^{24}$ and $R^{25}$ independently of one another very particularly preferably represent hydrogen, fluorine, chlorine, bromine or methyl.

$R^{24}$ and $R^{25}$ especially preferably each represent hydrogen.

$R^{26}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{26}$ particularly preferably represents hydrogen, fluorine, chlorine, bromine, iodine, methyl, ethyl, trifluoromethyl, difluoromethyl, difluorochloromethyl or trichloromethyl.

$R^{26}$ very particularly preferably represents hydrogen, fluorine, chlorine, bromine, methyl or trifluoromethyl.

$R^{26}$ especially preferably represents methyl or trifluoromethyl.

$R^{27}$ and $R^{28}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{27}$ and $R^{28}$ independently of one another particularly preferably represent hydrogen, fluorine, chlorine, bromine, nitro, methyl, ethyl, trifluoromethyl, difluoromethyl, difluorochloromethyl or trichloromethyl.

$R^{27}$ and $R^{28}$ independently of one another very particularly preferably represent hydrogen, fluorine, chlorine, bromine, methyl, trifluoromethyl, difluoromethyl or trichloromethyl.

$R^{27}$ and $R^{28}$ especially preferably each represent hydrogen.

$R^{29}$ preferably represents fluorine, chlorine, bromine, methyl, ethyl or $C_1$-$C_2$-haloalkyl having 1 to 5 fluorine, chlorine and/or bromine atoms.

$R^{29}$ particularly preferably represents fluorine, chlorine, bromine, methyl, ethyl, trifluoromethyl, difluoromethyl, difluorochloromethyl or trichloromethyl.

$R^{29}$ very particularly preferably represents fluorine, chlorine, bromine, methyl, trifluoromethyl, difluoromethyl or trichloromethyl.

$R^{29}$ especially preferably represents methyl.

$R^{30}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{30}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{30}$ very particularly preferably represents hydrogen, fluorine, chlorine, bromine, amino, methylamino, dimethylamino, methyl, trifluoromethyl, difluoromethyl or trichloromethyl.

$R^{30}$ especially preferably represents amino, methylamino, dimethylamino, methyl or trifluoromethyl.

$R^{31}$ preferably represents fluorine, chlorine, bromine, hydroxyl, methyl, ethyl, methoxy, ethoxy, cyclopropyl, $C_{1-2}$-haloalkyl or $C_1$-$C_2$-haloalkoxy having 1 to 5 fluorine, chlorine and/or bromine atoms.

$R^{31}$ particularly preferably represents fluorine, chlorine, bromine, hydroxyl, methyl, ethyl, methoxy, ethoxy, cyclopropyl, trifluoromethyl, difluoromethyl, difluorochloromethyl or trichloromethyl.

$R^{31}$ very particularly preferably represents fluorine, chlorine, bromine, hydroxyl, methyl, methoxy, cyclopropyl, trifluoromethyl, difluoromethyl or trichloromethyl.

$R^{32}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{32}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{32}$ very particularly preferably represents hydrogen, fluorine, chlorine, bromine, amino, methylamino, dimethylamino, methyl, trifluoromethyl, difluoromethyl or trichloromethyl.

$R^{32}$ especially preferably represents amino, methylamino, dimethylamino, methyl or trifluoromethyl.

$R^{33}$ preferably represents fluorine, chlorine, bromine, methyl, ethyl or $C_1$-$C_2$-haloalkyl having 1 to 5 fluorine, chlorine and/or bromine atoms.

$R^{33}$ particularly preferably represents fluorine, chlorine, bromine, methyl, ethyl, trifluoromethyl, difluoromethyl, difluorochloromethyl or trichloromethyl.

$R^{33}$ very particularly preferably represents fluorine, chlorine, bromine, methyl, trifluoromethyl, difluoromethyl or trichloromethyl.

$R^{33}$ especially preferably represents methyl, trifluoromethyl or difluoromethyl.

$R^{34}$ preferably represents hydrogen, methyl or ethyl.

$R^{34}$ particularly preferably represents methyl.

$R^{35}$ preferably represents fluorine, chlorine, bromine, methyl, ethyl, trifluoromethyl or difluoromethyl.

R³⁵ particularly preferably represents fluorine, chlorine, methyl, trifluoromethyl or difluoromethyl.
R³⁶ preferably represents hydrogen, fluorine, chlorine, bromine, methyl, ethyl or $C_1$-$C_2$-haloalkyl having 1 to 5 fluorine, chlorine and/or bromine atoms.
R³⁶ particularly preferably represents hydrogen, fluorine, chlorine, bromine, methyl or trifluoromethyl.
R³⁷ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.
R³⁷ particularly preferably represents fluorine, chlorine, bromine, iodine, methyl, ethyl, n-propyl, isopropyl, n-butyl, iso-butyl, sec-butyl, tert-butyl, trifluoromethyl, difluoromethyl, difluorochloromethyl, trichloromethyl.
R³⁷ very particularly preferably represents fluorine, chlorine, bromine, iodine, methyl, trifluoromethyl, difluoromethyl or trichloromethyl.
R³⁸ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.
R³⁸ particularly preferably represents hydrogen, methyl, ethyl, trifluoromethyl, methoxymethyl, ethoxymethyl, hydroxymethyl or hydroxyethyl.
R³⁸ very particularly preferably represents methyl or methoxymethyl.
R³⁹ preferably represents hydrogen, fluorine, chlorine, bromine, methyl, ethyl or $C_1$-$C_2$-haloalkyl having 1 to 5 fluorine, chlorine and/or bromine atoms.
R³⁹ particularly preferably represents hydrogen, fluorine, chlorine, bromine, methyl, ethyl, trifluoromethyl, difluoromethyl or trichloromethyl.
R³⁹ vera particularly preferably represents hydrogen or methyl.
R⁴⁰ represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.
R⁴⁰ particularly preferably represents hydrogen, fluorine, chlorine, bromine, iodine, cyano, methyl, ethyl, isopropyl, trifluoromethyl, difluoromethyl, difluorochloromethyl or trichloromethyl.
R⁴⁰ very particularly preferably represents hydrogen, iodine, methyl or trifluoromethyl.
R⁴¹ preferably represents hydrogen, fluorine, chlorine, bromine, methyl, ethyl or $C_1$-$C_2$-haloalkyl having 1 to 5 fluorine, chlorine and/or bromine atoms.
R⁴¹ particularly preferably represents hydrogen, fluorine, chlorine, bromine, iodine, methyl or trifluoromethyl.
R⁴¹ very particularly preferably represents hydrogen or trifluoromethyl.
R⁴² preferably represents fluorine, chlorine, bromine, iodine, methyl, ethyl, n-propyl, isopropyl, trifluoromethyl or difluoromethyl.
R⁴² particularly preferably represents fluorine, chlorine, bromine, iodine, methyl, ethyl or trifluoromethyl.
R⁴³ preferably represents methyl, ethyl or $C_1$-$C_2$-haloalkyl having 1 to 5 fluorine, chlorine and/or bromine atoms.
R⁴³ particularly preferably represents methyl, ethyl, trifluoromethyl, difluoromethyl, difluorochloromethyl or trichloromethyl.
R⁴⁴ preferably represents methyl or ethyl.
R⁴⁴ particularly preferably represents methyl.
$Q^1$ preferably represents S (sulphur), $SO_2$ or $CH_2$.
$Q^1$ particularly preferably represents S (sulphur) or $CH_2$.

$Q^1$ very particularly preferably represents S (sulphur).
p preferably represents 0 or 1.
p particularly preferably represents 0.

Emphasis is given to compounds of the formula (I), in which R¹ is hydrogen.

Emphasis is given to compounds of the formula (I), in which R¹ is formyl.

Emphasis is furthermore given to compounds of the formula (I), in which R⁴ is —C(=O)C(=O)R⁵, where R⁵ is as defined above.

Emphasis is given to compounds of the formula (I), in which A is A1.

Emphasis is given to compounds of the formula (I), in which M is M-1.

Emphasis is furthermore given to compounds of the formulae

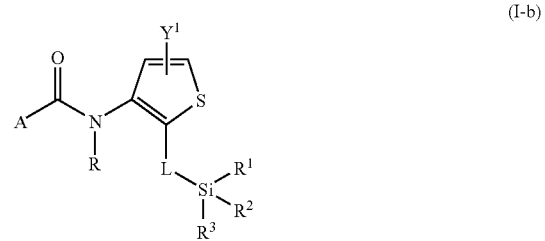

(I-b)

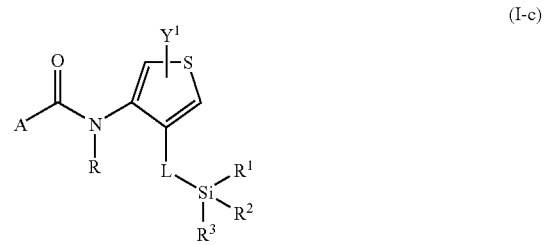

(I-c)

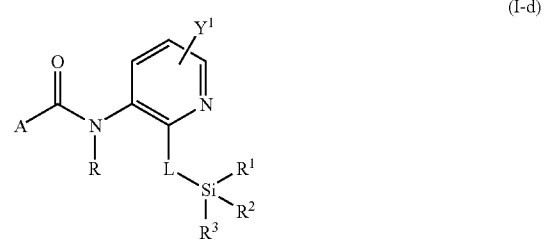

(I-d)

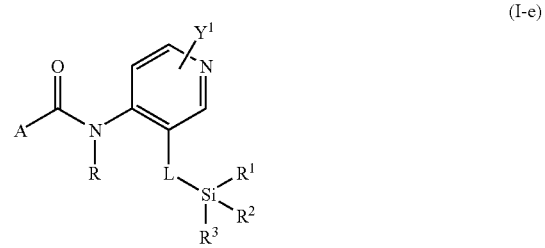

(I-e)

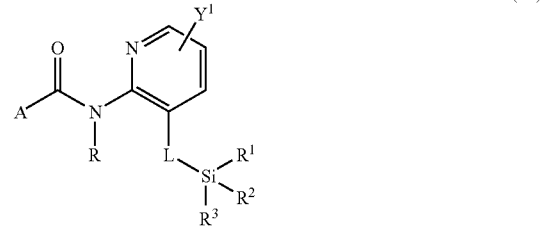

(I-f)

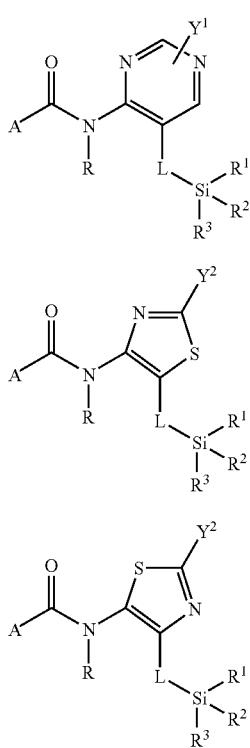

(I-g)

(I-h)

(I-i)

in which in each case $Y^1$, $Y^2$, L, $R^1$, $R^2$, $R^3$, R and A have the general, preferred, particularly preferred, very particularly preferred, etc. meanings given above.

Saturated or unsaturated hydrocarbon radicals, such as alkyl or alkenyl, can in each case be straight-chain or branched, as far as this is possible, including combinations with heteroatoms, such as, for example, in alkoxy.

Optionally substituted radicals may be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen denotes fluorine, chlorine, bromine and iodine, in particular fluorine, chlorine and bromine.

The general or preferred radical definitions or illustrations given above can be combined between the respective ranges and preferred ranges as desired. The definitions apply both to the end products and, correspondingly, to the precursors and intermediates.

The definitions mentioned can be combined with one another as desired. Moreover, individual definitions may not apply.

Preferred, particularly preferred or very particularly preferred are compounds of the formula (I) carrying the substituents mentioned in each case under preferred, particularly preferred and very particularly preferred, respectively.

Descriptions of the Processes and Intermediates

Process (a)

Using 2-chlorobenzoyl chloride and {2-[1-methyl-2-trimethylsilyl)ethyl]-3-thienyl}amine as starting materials, the process (a) according to the invention can be illustrated by the formula scheme below:

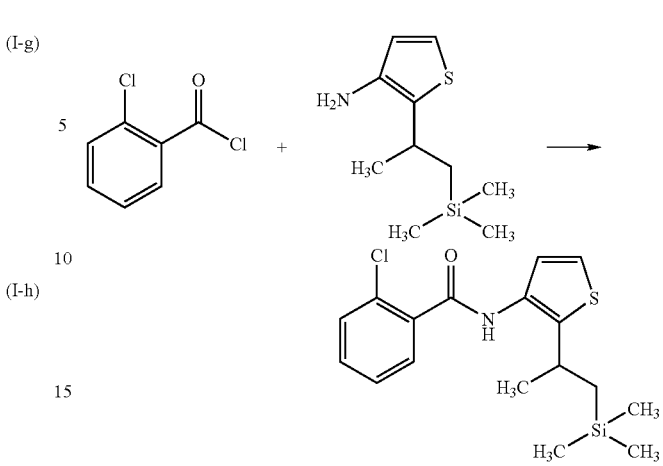

The formula (II) provides a general definition of the carboxylic acid derivatives required as starting materials for carrying out the process (a) according to the invention. In this formula (II), A preferably, particularly preferably and very particularly preferably has those meanings which have already been mentioned in connection with the description of the compounds of the formula (I) as being preferred, particularly preferred and very particularly preferred, respectively, for A. $X^1$ preferably represents chlorine, bromin or hydroxyl.

Carboxylic acid derivatives of the formula (II) are known and/or can be obtained by known methods (cf. WO 93/11117, EP-A 0 545 099, EP-A 0 589 301 and EP-A 0 589 313).

The formula (III) provides a general definition of the amines furthermore required as starting materials for carrying out the process (a) according to the invention. In this formula (III), M, L, $R^1$, $R^2$ and $R^3$ preferably, particularly preferably and very particularly preferably have those meanings which have already been mentioned in connection with the description of the compounds of the formula (I) according to the invention as being preferred, particularly preferred and very particularly preferred, respectively, for these radicals.

The amines of the formula (III) are novel.

Amines of the formula (III-a)

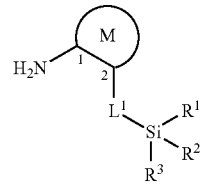

(III-a)

in which
$L^1$ represents alkylene (alkanediyl),
M, $R^1$, $R^2$ and $R^3$ are as defined above
are obtained, for example, by reacting
c) protected amines of the formula (V)

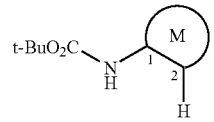

(V)

in which M and R are as defined above,
in a first step with an iodinating agent (for example iodine), if appropriate in the presence of a diluent (for example tetrahydrofuran) and if appropriate in the presence of an organometallic compound (for example n-butyllithium),
and reacting the resulting iodides of the formula (VI)

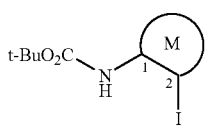
(VI)

in which M and R are as defined above,
in a second step with compounds of the formula (VII)

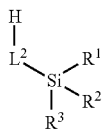
(VII)

in which
$L^2$ represents alkenylene (alkenediyl) or alkynylene (alkynediyl),
$R^1$, $R^2$ and $R^3$ are as defined above
in the presence of a base (for example triethylamine), in the presence of a catalyst [for example bis(triphenylphosphine)palladium(II) chloride] and if appropriate in the presence of further reaction auxiliaries [for example copper(I) iodide],
and hydrogenating the resulting protected amines of the formula (VIII)

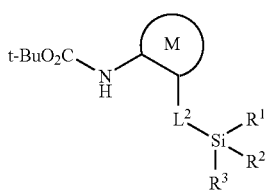
(VIII)

in which M, $L^2$, $R^1$, $R^2$ and $R^3$ are as defined above
in a third step in the presence of a catalyst (for example palladium) and if appropriate in the presence of a diluent (for example methanol),
and reacting the resulting protected amines of the formula (IX)

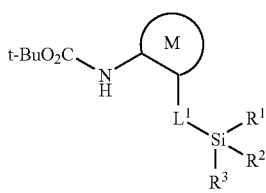
(IX)

in which M, $L^1$, $R^1$, $R^2$ and $R^3$ are as defined above
in a fourth step in the presence of an acid (for example trifluoroacetic acid) and if appropriate in the presence of a diluent
(cf. also the Preparation Examples).

Amines of the formula (III-b)

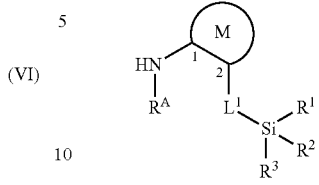
(III-b)

in which M, $L^1$, $R^1$, $R^2$, $R^3$ and $R^4$ are as defined above
are obtained by reacting
amines of the formula (III-a) with halides of the formula (IV)

(IV)

in which $X^2$ and $R^4$ are as defined above,
according to process (b).
Amines of the formula (III-b) can also be obtained by initially reacting amines of the formula (IX) with halides of the formula (IV) and then removing the protective group [according to step 4 from process (c)].
Amines of the formula (III-c)

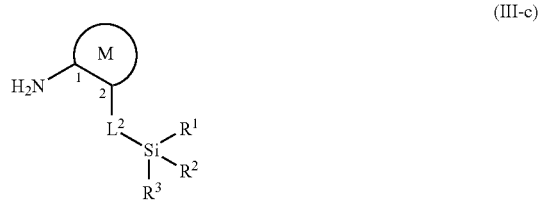
(III-c)

in which M, $L^2$, $R^1$, $R^2$ and $R^3$ are as defined above
are obtained by deprotecting protected amines of the formula (VIE) [according to step 4 from process (c)].
Amines of the formula (III-d)

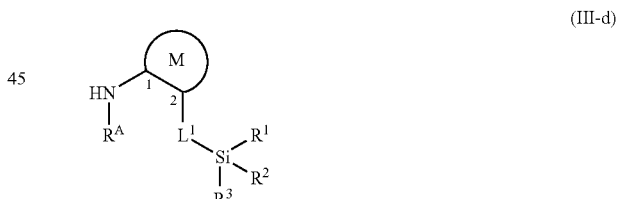
(III-d)

in which M, $L^1$, $R^1$, $R^2$, $R^3$ and $R^4$ are as defined above
are obtained by reacting amines of the formula (IE-c) with halides of the formula (IV), analogously to process (b), or by reacting protected amines of the formula (VI) with halides of the formula (IV), followed by removal of the protective group [according to step 4 from process (c)].
Amines of the formula (III) can furthermore be obtained analogously to the description in WO 03/080628.
In the formulae (III-a), (III-b), (III-c), (III-d), (VII), (VIII) and (IX), $L^1$ and $L^2$ preferably, particularly preferably and very particularly preferably have the corresponding preferred, particularly preferred and very particularly preferred meanings mentioned in each case for L.
Process (b)
Using 5-fluoro-1,3-dimethyl-N-{2-[2-(trimethylsilyl)ethyl]-3-thienyl}-1H-pyrazole-4-carboxamide and ethyl chloro(oxo)acetate as starting materials, the course of the process (b) according to the invention can be illustrated by the formula scheme below:

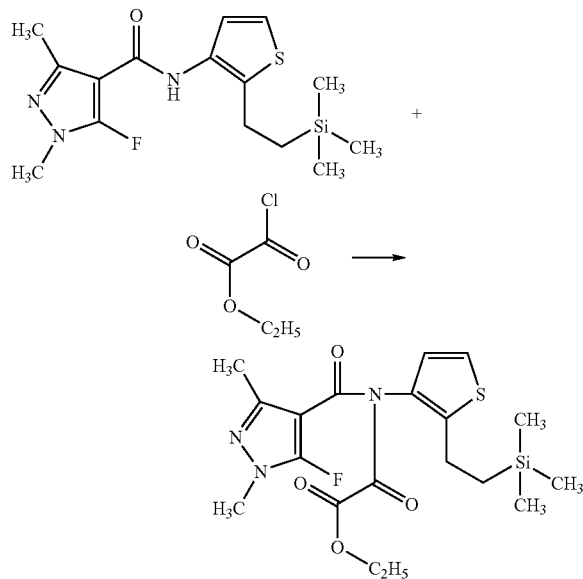

The formula (I-a) provides a general definition of the silylated carboxamides required as starting materials for carrying out the process (b) according to the invention. In this formula (I-a), M, L, A, $R^1$, $R^2$ and $R^3$ preferably, particularly preferably and very particularly preferably have those meanings which have already been mentioned in connection with the description of the compounds of the formula (I) according to the invention as being preferred, particularly preferred and very particularly preferred, respectively, for these radicals.

The silylated carboxamides of the formula (I-a) are likewise compounds according to the invention and also form part of the subject-matter of this application. They can be obtained by the process (a) according to the invention (where R=hydrogen).

The formula (IV) provides a general definition of the halides furthermore required as starting materials for carrying out the process (b) according to the invention.

$R^4$ preferably represents $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-$C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^4$, —CONR$^5$R$^6$ or CH$_2$NR$^7$R$^8$.

$R^4$ particularly preferably represents methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CCl$_3$, —CH$_2$—CO—CH$_2$CF$_3$, —CH$_2$—CO—CH$_2$CCl$_3$, —(CH$_2$)$_2$—CO—H$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^4$, —CONR$^5$R$^6$ or —CH$_2$NR$^7$R$^8$.

$R^A$ very particularly preferably represents methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$X^2$ preferably represents chlorine or bromine.

Halides of the formula (I) are known.

Reaction Conditions

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (a) according to the invention is, if appropriate, carried out in the presence of a suitable condensing agent. Suitable condensing agents are all condensing agents customarily used for such amidation reactions. Examples which may be mentioned are acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphospine/carbon tetrachloride or bromotripyrrolidinophosphonium hexafluorophosphate.

Process (a) according to the invention is, if appropriate, carried out in the presence of a catalyst. Examples which may be mentioned are 4-dimethylaminopyridine, 1-hydroxybenzotriazole or dimethylformamide.

When carrying out the process (a) according to the invention, the reaction temperatures may be varied within a relatively wide range. In general, the process is carried out at temperatures from 0° C. to 150° C., preferably at temperatures of from 0° C. to 80° C.

For carrying out the process (a) according to the invention for preparing the compounds of the formula (I), in general from 0.2 to 5 mol, preferably from 0.5 to 2 mol, of aniline derivative of the formula (III) are employed per mole of the carboxylic acid derivative of the formula (II).

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (b) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-methylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (b) according to the invention, the reaction temperatures can be varied within a relatively wide range. In general, the process is carried out at temperatures of from 0° C. to 150° C., preferably at temperatures of from 20° C. to 110° C.

For carrying out process (b) according to the invention for preparing the compounds of the formula (I), in general from 0.2 to 5 mol, preferably from 0.5 to 2 mol, of halide of the formula (IV) are employed per mole of the isopentylcarboxanilide of the formula (I-a).

Unless indicated otherwise, all processes according to the invention are generally carried out under atmospheric pressure. However, it is also possible to operate under elevated or reduced pressure—in general between 0.1 bar and 10 bar.

The compounds according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea*

(conidia form: *Drechslera*, syn: *Helminthosporium*);

*Cochliobolus* species, such as, for example, *Cochliobolus sativus*

(conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasalii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*
*Alternaria* species, such as, for example, *Alternaria brassicae;* and
*Pseudocercosporella* species, such as, for example, *Pseudocercosporella herpotrichoides.*
*Rhizoctonia* species, such as, for example, *Rhizoctonia solani.*

The active compounds according to the invention also show a strong invigorating action in plants. Accordingly, they are suitable for mobilizing the internal defenses of the plant against attack by unwanted microorganisms.

In the present context, plant-invigorating (resistance-inducing) compounds are to be understood as meaning substances which are capable of stimulating the defense system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed with particularly good results for controlling cereal diseases, such as, for example, against *Puccinia* species, and of diseases in viticulture and in the cultivation of fruit and vegetables, such as, for example, against *Botrytis, Venturia* or *Alternaria* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
*Alternaria*, such as *Alternaria tenuis,*
*Aspergillus*, such as *Aspergillus niger,*
*Chaetomium*, such as *Chaetomium globosum,*
*Coniophora*, such as *Coniophora puetana,*
*Lentinus*, such as *Lentinus tigrinus,*
*Penicillium*, such as *Penicillium glaucum,*
*Polyporus*, such as *Polyporus versicolor,*
*Aureobasidium*, such as *Aureobasidium pullulans,*
*Sclerophoma*, such as *Sclerophoma pityophila,*
*Trichoderma*, such as *Trichoderma viride,*
*Escherichia*, such as *Escherichia coli,*
*Pseudomonas*, such as *Pseudomonas aeruginosa*, and
*Staphylococcus*, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:
Fungicides:
2-phenylphenol; 8-hydroxyquinoline sulphate; acibenzolar-S-methyl; aldimorph; amidoflumet; ampropylfos; anpropylfos-potassium; andoprim; anilazine; azaconazole; azoxystrobin; benalaxyl; benalaxyl-M; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover, flumorph; fluoromnide; fluoxastrobin; fluquinconazole; flurprimidol; flusilazole; flusulphamide; flutolanil; flutriafol; folpet; fosetyl-A1; fosetyl-sodium; fuberidazole; furalaxyl; furametpyr, furcarbanil; furmecyclox; guazatine; hexachlorobenzene; hexaconazole; hymexazole; imazalil; iniubenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metirar; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procyrnidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
1. Acetylcholinesterase (AChE) Inhibitors
1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulphan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
1.2 organophosphate (for example acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl-ethyl), coumaphos, cyanofenphos, cyanophos, chlorfenvinphos, demeton-s-methyl, demeton-s-methylsulphon, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulatorsblockers of Voltage-Dependent Sodium Channels
2.1 pyrethroide (for example acrinathrin, allethrin (d-cis-trans, d-trans), beta-cyfluthrin, bifenthrin, bioallethrin, bioallethirin-s-cyclopentyl-isomer, bioethanomethrin, biopermethrin, bioresmethrin, chlovaporthrin, cis-cypermethrin, cis-resmethrin, cis-permethrin, clocythrin, cyloprothrin, cyflutirin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))
2.2 oxadiazines (for example indoxacarb)

3. Acetylcholine Receptor Agonists/Antagonists
3.1 chloronicotinyls/neonicotinoids (for example acetamiprid, clothianidin, dinotefuran, imidacloprid, nitenpyram, nithiazine, thiacloprid, thiamethoxam)
3.2 nicotine, bensultap, cartap 4. Acetylcholine Receptor Modulators
4.1 spinosyns (for example spinosad)

5. Antagonists of GABA-Controlled Chloride Channels
5.1 cyclodiene organochlorines (for example camphechlor, chlordane, endosulphan, gamma-HCH, HCH, heptachlor, lindane, methoxychlor
5.2 fiproles (for example acetoprole, ethiprole, fipronil, vaniliprole)

6. Chloride Channel Activators
6.1 mectins (for example abamectin, avermectin, emamectin, emamectin-benzoate, ivermectin, milbemectin, milbemycin)

7. Juvenile Hormone Mimetics
(for example diofenolan, epofenonane, fenoxycarb, hydroprene, kinoprene, methoprene, pyriproxifen, triprene)

8. Ecdyson Agonists/Disruptors
8.1 diacylhydrazine (for example chromafenozide, halofenozide, methoxyfenozide, tebufenozide)

9. Chitin Biosynthesis Inhibitors
9.1 benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)
9.2 buprofezin
9.3 cyromazine 10. Inhibitors of Oxidative Phosphorylation, ATP Disruptors
10.1 diafenthiuron
10.2 organotins (for example azocyclotin, cyhexatin, fenbutatin-oxide)

11. Decouplers of Oxidative Phosphorylation Acting by Interrupting the H-Proton Gradient
11.1 pyrroles (for example chlorfenapyr)
11.2 dinitrophenole (for example binapacyrl, dinobuton, dinocap, DNOC)

12. Side-I Electron Transport Inhibitors
12.1 METIs (for example fenazaquin, fenpyroximate, pyrimidifen, pyridaben, tebufenpyrad, tolfenpyrad)
12.2 hydramethylnone
12.3 dicofol 13. Side-II Electron Transport Inhibitors
13.1 rotenone 14. Side-III Electron Transport Inhibitors
14.1 acequinocyl, fluacrypyrim 15. Microbial Disruptors of the Insect Gut Membrane
*Bacillus thuringiensis* strains 16. Inhibitors of Fatty Synthesis
16.1 tetronic acids (for example spirodiclofen, spiromesifen)
16.2 tetraic acids [for example 3-2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-2,5-dimethylphenyl)-8-methoxy-2-oxo-1-azaspiro[4.5]dec-3-en-4-yl ethyl ester (CAS-Reg.-No.: 203313-25-1)]

17. Carboxamides
(for example flonicamid)

18. Octopaminergic Agonists
(for example amitraz)

19. Inhibitors of Magnesium-Stimulated ATPASE
(for example propargite)

20. Phthalamide
(for example $N^2$-[, 1-dimethyl-2-methylsulphonyl)ethyl]-3-iodo-N'-[2-methyl-4-[1,2,2,2-tetrafluoro-1-(trifluoromethyl)ethyl]phenyl]-1,2-benzenedicarboxamide (CAS-Reg.-No.: 272451-65-7), flubendiamide)

21. Nereistoxin Analogues
(for example thiocyclam hydrogen oxalate, thiosultap-sodium)

22. Biologicals, Hormones or Pheromones
(for example azadirachtin, *Bacillus* spec., *Beauveria* spec., *Codlemone*, *Metarrhizium* spec., *Paecilomyces* spec., *Thuringiensin*, *Verticillium* spec.)

23. Active Compounds with Unknown or Unspecific Mechanisms of Action
23.1 fumigants (for example aluminium phosphide, methyl bromide, sulphuryl fluoride)
23.2 selective antifeedants (for example cryolite, flonicamid, pymetrozine)
23.3 mite growth inhibitors (for example clofentezine, etoxazole, hexythiazox)
23.4 amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprolei pyridalyl, pyriprole, sulfluramid, tetradifon, tetrasul, triarathene, verbutin, furthermore the compound 3-methylphenylpropylcarbamate (tsumacide Z3, the compound 3-(5-chloro-3-pyridinyl)-8-2, 2,2-trifluoroethyl)-8-azabicyclo[3.2.1]octane-3-carbonitrile (CAS-Reg.-No. 185982-80-3) and the corresponding 3-endo-isomer (CAS-Reg.-No. 18598460-5) (cf. WO 96/37494, WO 98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidernophyton floccosur, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5 000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Boligard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

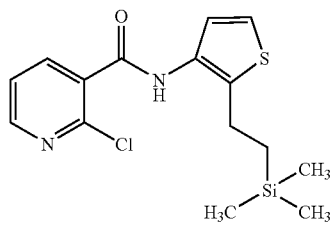

183 mg (1.3 mmol) of potassium carbonate and 443 mg (2.1 mmol) of 2-chloronicotinoyl chloride are added to a solution comprising 240 mg (1.2 mmol) of 2-[2-trimethylsilyl)ethyl]thiophene-3-amine in 15 ml of acetonitrile. After 16 h at room temperature, the reaction mixture is poured into water and extracted with ethyl acetate, and the extract is dried over sodium sulphate and concentrated under reduced pressure. Column chromatography (gradient cyclohexane/ethyl acetate) gives 100 mg (24% of theory) of 2-chloro-N-{2-[2-(trimethylsilyl)ethyl]-3-thienyl}nicotinamide [log P (pH 2.3)=3.65].

The compounds of the formula (I) listed in Table 1 below are obtained analogously to Example 1 and in accordance with the statements in the general descriptions of the process.

TABLE 1

| Ex. | A | M$^{a)}$ | R | L—Si(R$^1$R$^2$R$^3$) | logP (pH 2.3) |
|---|---|---|---|---|---|
| 2 | F$_3$C-pyrazole-CH$_3$ | thienyl | H | —(CH$_2$)$_2$—Si(CH$_3$)$_3$ | 3.85 |
| 3 | F$_2$HC-thiazole-CH$_3$ | thienyl | H | —(CH$_2$)$_2$—Si(CH$_3$)$_3$ | 4.01 |
| 4 | CF$_3$-phenyl | thienyl | H | —(CH$_2$)$_2$—Si(CH$_3$)$_3$ | 4.38 |
| 5 | F$_3$C-pyrrole-CH$_3$ | thienyl | H | —(CH$_2$)$_2$—Si(CH$_3$)$_3$ | 4.13 |

TABLE 1-continued (I), (I-b) structures

| Ex. | A | M | R | L—Si(R¹R²R³) | logP (pH 2.3) |
|---|---|---|---|---|---|
| 6 | F₂HC-(1-methyl-4-methylpyrazol-3-yl) | thiophene (*1, #2) | H | —(CH₂)₂—Si(CH₃)₃ | 3.66 |
| 7 | H₃C-(1-methyl-4-methyl-5-fluoropyrazol-3-yl) | thiophene (*1, #2) | H | —(CH₂)₂—Si(CH₃)₃ | 3.69 |
| 8 | I-(1-methyl-4-methylpyrazol-3-yl) | thiophene (*1, #2) | H | —(CH₂)₂—Si(CH₃)₃ | 3.72 |
| 9 | 2-(CF₃)-phenyl-methyl | pyridine (*1, #2) | H | —(CH₂)₂—Si(CH₃)₃ | 3.17 |
| 10 | F₃C-(1-methyl-4-methylpyrrol-3-yl) | 6-fluoropyridine (*1, #2) | H | —(CH₂)₂—Si(CH₃)₃ | 3.28 |
| 11 | 2-(CF₃)-phenyl-methyl | 6-fluoropyridine (*1, #2) | H | —(CH₂)₂—Si(CH₃)₃ | 3.78 |

TABLE 1-continued (I) and (I-b) general structures shown.

| Ex. | A | M[a)] | R | L—Si(R¹R²R³) | logP (pH 2.3) |
|---|---|---|---|---|---|
| 12 | F₂HC-(4,5-dimethyl-2-methyl-thiazol-yl) | pyridin-2,3-yl (*1, #2) | H | —(CH₂)₂—Si(CH₃)₃ | 3.78 |
| 13 | 2-chloro-3-methyl-pyridin-yl | pyridin-2,3-yl (*1, #2) | H | —(CH₂)₂—Si(CH₃)₃ | 2.32 |
| 14 | F₃C-(4,5-dimethyl-2-methyl-thiazol-yl) | thien-2,3-yl (*1, #2) | H | —(CH₂)₂—Si(CH₃)₃ | 4.29 |
| 15 | F₃C-(4,5-dimethyl-2-methyl-thiazol-yl) | pyridin-2,3-yl (*1, #2) | H | —(CH₂)₂—Si(CH₃)₃ | 3.68 |

[a)]The bond marked "*" is attached to the amide, the bond marked "#" is attached to the radical L.

Preparation of Starting Materials of the Formula (VI)

Example (VI-1)

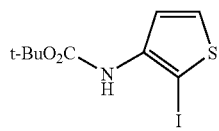

At —78° C., under an atmosphere of argon, 7.8 ml of n-BuLi (1.6 M in hexane, 0.013 mol) are added dropwise to a solution comprising 5.0 g (0.025 mol) of tert-butyl-N-(3-thienyl)carbamate in 50 ml of THF. After 30 min at −78° C., the reaction solution is warmed to −10° C., and a solution comprising 7.6 g (0.030 mol) of iodine in 20 ml of THF is added. After one hour at −10° C., the reaction mixture is warmed to room temperature, poured into water and extracted with ethyl acetate, and the extract is dried over sodium sulphate and concentrated under reduced pressure. Column chromatography (cyclohexane/ethyl acetate 10:1) gives 4.8 g (59% of theory) of tert-butoxy (2-iodothiophen-3-yl)-carbamate.

¹H-NMR (CD₃CN): δ=1.48 (s, 9H), 6.87 (broad s, 1H), 7.22 (d, 1H), 7.55 (d, 1H) ppm.

Preparation of Starting Materials of the Formula (VIII)

Example (VIII-1)

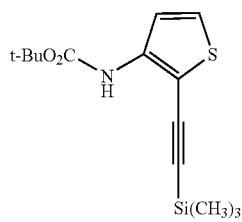

Under protective gas (argon), 4.8 g (0.015 mol) of tert-butoxy (2-iodothiophen-3-yl)carbamate (VI-1) are dissolved in 50 ml of triethylamine, and 622 mg (0.89 mmol) of bis(triphenylphosphine)-palladium(II) chloride, 169 mg (0.89 mmol) of copper(I) iodide and 2.2 g (0.022 mmol) of trimethylsilylacetylene are added. The reaction mixture is stirred at room temperature for 14 h and then added to water and extracted with ethyl acetate, and the extract is dried over sodium sulphate and concentrated under reduced pressure. Column chromatography (cyclohexane/ethyl acetate 10:1) gives 3.7 g (84% of theory) tert-butyl {2-[(trimethylsilyl)ethynyl]-3-thienyl}carbamate.

$^1$H-NMR (CD$_3$CN): δ=0.06 (s, 9H), 1.31 (s, 9H), 7.08 (broad s, 1H), 7.10 (d, 1H), 7.30 (d, 1H) ppm.

Preparation of Starting Materials of the Formula (IX)

Example (IX-1)

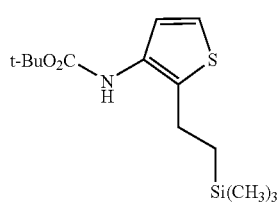

In an autoclave, a reaction mixture comprising 2.9 g (9.8 mmol) of tert-butyl {2-[(trimethylsilyl)ethynyl]-3-thienyl}carbamate (VIII-1) in 50 ml of methanol and 800 mg of palladium (5% on carbon) is hydrogenated under 8 bar of hydrogen for 10 h and, after addition of a further 800 mg of palladium (5% on carbon), for a further 10 h (8 bar of hydrogen). The reaction mixture is filtered through silica gel and concentrated under reduced pressure, which gives 2.8 g (95% of theory) of tert-butoxy[2-(2-trimethylsilanylethyl)thiophen-3-yl]carbamate.

$^1$H-NMR (CD$_3$CN): δ=0.04 (s, 9H), 0.85-0.90 (m, 2H), 2.64-2.70 (m, 2H), 1.49 (s, 9H), 6.89 (broad s, 1H), 7.02-7.06 (m, 2H) ppm.

Preparation of Starting Materials of the Formula (III)

Example (III-1)

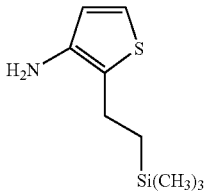

5 ml of trifluoroacetic acid are added to a solution consisting of 2.8 g (9.3 mmol) of tert-butoxy[2-(2-trimethylsilanylethyl)thiophen-3-yl]carbamate (IX-1) in 50 ml of dichloromethane. The reaction solution is stirred at room temperature for 3 h and then concentrated under reduced pressure. Column chromatography (gradiant cyclohexane/ethyl acetate 4:1 to 1:1) gives 1.2 g (65% of theory) of 2-(2-trimethylsilanylethyl)thiophen-3-ylamine [log P (pH 2.3)=1.78].

The given log P values were determined in accordance with EEC Directive 79/831 Annex V.A8 by HPLC (High Performance Liquid Chromatography) on a reversed-phase column (C 18). Temperature: 43° C. Mobile phases for the determination in the acidic range (pH 2.3): 0.1% aqueous phosphoric acid, acetonitrile; linear gradient from 10% acetonitrile to 90% acetonitrile. Calibration was carried out using unbranched alkan-2-ones (having 3 to 16 carbon atoms) with known logP values (determination of the logP values by the retention times using linear interpolation between two successive alkanones). The lambda max values were determined in the maxima of the chromatographic signals using the UV spectra from 200 nm to 400 nm.

USE EXAMPLES

Example A

| | Podosphaera test (apple)/protective |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

TABLE A

*Podosphaera* test (apple)/protective

| Active compound according to the invention | Application rate of active compound in g/ha | Efficacy in % |
|---|---|---|
| 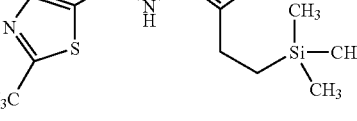 | 100 | 100 |
| 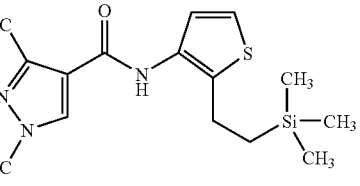 | 100 | 100 |
| 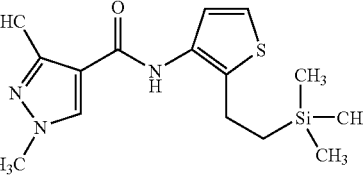 | 100 | 100 |
| 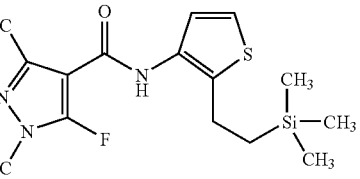 | 100 | 100 |
| 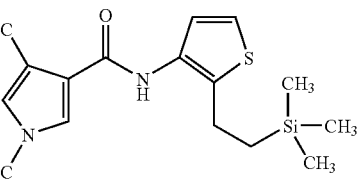 | 100 | 99 |

Example B

*Sphaerotheca* test (cucumber)/protective

| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation was carried out 7 days after the inoculation. 0% means an efficacy which corresponds to that of the control, whereas an efficacy of 100% means that no infection is observed.

TABLE B

*Sphaerotheca* test (cucumber)/protective

| Active compound according to the invention | Application rate of active compound in g/ha | Efficacy in % |
|---|---|---|
| 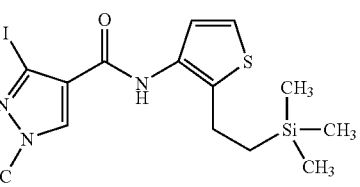 | 100 | 100 |
| | 100 | 100 |
| | 100 | 100 |
| | 100 | 100 |
| | 100 | 100 |
|  | 100 | 98 |

Example C

Venturia test (apple)/protective

| Solvents: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE C

*Venturia* test (apple)/protective

| Active compound according to the invention | Application rate of active compound in g/ha | Efficacy in % |
| --- | --- | --- |
| [structure: F2HC-thiazole-C(O)NH-thiophene-CH2CH2-Si(CH3)2-CH3, with H3C on thiazole] | 100 | 100 |
| [structure: F3C-pyrazole(N-CH3)-C(O)NH-thiophene-CH2CH2-Si(CH3)2-CH3] | 100 | 100 |
| [structure: F2HC-pyrazole(N-CH3)-C(O)NH-thiophene-CH2CH2-Si(CH3)2-CH3] | 100 | 100 |
| [structure: H3C-pyrazole(F, N-CH3)-C(O)NH-thiophene-CH2CH2-Si(CH3)2-CH3] | 100 | 100 |
| [structure: F3C-pyrrole(N-CH3)-C(O)NH-thiophene-CH2CH2-Si(CH3)2-CH3] | 100 | 99 |
| [structure: I-pyrazole(N-CH3)-C(O)NH-thiophene-CH2CH2-Si(CH3)2-CH3] | 100 | 100 |

Example D

Botrytis test (bean)/protective

| Solvents: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% atmospheric humidity.

The size of the infected areas of the leaves is evaluated 2 days after the inoculation. 0% means an efficacy which corresponds to that of the control, whereas an efficacy of 100% means that no infection is observed.

TABLE D

Botrytis-Test (bean)/protective

| Active compound according to the invention | Application rate of active compound in g/ha | Efficacy in % |
|---|---|---|
| F₂HC-thiazole-C(=O)NH-thiophene-CH₂CH₂-Si(CH₃)₃ (2-methyl-thiazole) | 500 | 100 |
| F₃C-pyrazole(N-CH₃)-C(=O)NH-thiophene-CH₂CH₂-Si(CH₃)₃ | 500 | 100 |
| F₂HC-pyrazole(N-CH₃)-C(=O)NH-thiophene-CH₂CH₂-Si(CH₃)₃ | 500 | 100 |
| H₃C-pyrazole(N-CH₃, 5-F)-C(=O)NH-thiophene-CH₂CH₂-Si(CH₃)₃ | 500 | 100 |
| F₃C-pyrrole(N-CH₃)-C(=O)NH-thiophene-CH₂CH₂-Si(CH₃)₃ | 500 | 100 |
| I-pyrazole(N-CH₃)-C(=O)NH-thiophene-CH₂CH₂-Si(CH₃)₃ | 500 | 100 |

Example E

Puccinia test (wheat)/protective

| | |
|---|---|
| Solvents: | 50 parts by weight of N,N-dimethylacetamide |
| Emulsifier: | 1 part by weight of alkylarylpolyglykolether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE E

Puccinia test (wheat)/protective

| Active compound according to the invention | Application rate of active compound in g/ha | Efficacy in % |
|---|---|---|
| F₂HC-thiazole(2-CH₃)-C(=O)NH-thiophene-CH₂CH₂-Si(CH₃)₃ | 500 | 100 |
| F₃C-pyrazole(N-CH₃)-C(=O)NH-thiophene-CH₂CH₂-Si(CH₃)₃ | 500 | 100 |
| F₂HC-pyrazole(N-CH₃)-C(=O)NH-thiophene-CH₂CH₂-Si(CH₃)₃ | 500 | 100 |
| H₃C-pyrazole(N-CH₃, 5-F)-C(=O)NH-thiophene-CH₂CH₂-Si(CH₃)₃ | 500 | 100 |

Example F

In Vitro Test for the $ED_{50}$ Determination in Microorganisms

A methanolic solution of the active compound to be tested, admixed with emulsifier PS16, is pipetted into the wells of a microtitre plate. After the solvent has evaporated, 200 µl of potato dextrose medium are added to each well. Beforehand, a suitable concentration of spores or mycelium of the fungus to be tested was added to the medium. The resulting concentrations of active compound are 0.05, 0.5, 5 and 50 ppm. The resulting concentration of the emulsifier is 300 ppm.

The plates are then incubated on a shaker at a temperature of 20° C. for 3-5 days, until sufficient growth can be observed in the untreated control.

Evaluation is carried out photometrically at a wavelength of 620 nm. The dose of active compound which causes 50% inhibition of fungal growth compared to the untreated control ($ED_{50}$) is calculated from data measured at different concentrations.

TABLE F

In vitro test for the $ED_{50}$ determination in microorganisms

| Active compound according to the invention | Microorganism | $ED_{50}$ value |
|---|---|---|
| ![structure] | *Alternaria mali* | <0.05 |
| ![structure] | *Alternaria mali* | <0.05 |
| ![structure] | *Aiternaria mali* | <0.05 |
| ![structure] | *Alternaria mali* | <0.05 |
| ![structure] | *Alternaria mali* | <0.05 |
| ![structure] | *Alternaria mali* | <0.05 |

The invention claimed is:

1. A method for controlling phytopathogenic fungi, comprising applying to the fungi, their habitat, or a combination thereof a silylated carboxamide of formula (I):

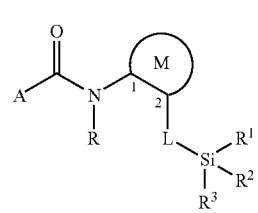

(I)

wherein
M represents a thiophine, monosubstituted by $Y^1$,
$Y^1$ represents hydrogen, fluorine, chlorine, bromine, methyl, isopropyl, methylthio or trifluoromethyl,
L represents a direct bond or represents straight-chain or branched alkylene (alkanediyl), alkenylene (alkenediyl) or alkynylene (alkynediyl), each of which is optionally substituted,
$R^1$, $R^2$ and $R^3$ are all methyl,
R represents hydrogen, or $C_1$-$C_8$-alkyl,
A represents the radical of the formula (A10)

(A10)

in which
$R^{30}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms, and
$R^{31}$ represents halogen, hydroxyl, $C_1$-$C_4$-alkyl, $C_1$-$C_4$-alkoxy, $C_3$-$C_6$-cycloalkyl, $C_1$-$C_4$-haloalkyl or $C_1$-$C_4$-haloalkoxy having in each case 1 to 5 halogen atoms.

2. The method of claim 1, wherein:

M represents one of the following heterocycles:

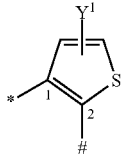 M-1

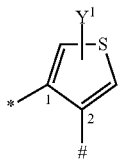 M-2

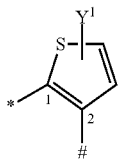 M-3 where the bond marked "*" is attached to the amide and the bond marked "#" is attached to the radical L, $Y^1$ represents hydrogen, fluorine, chlorine, methyl, isopropyl, methylthio or trifluoromethyl, L represents a direct bond or represents optionally halogen-substituted straight-chain or branched $C_1$-$C_6$-alkylene, $C_2$-$C_6$-alkenylene or $C_2$-$C_6$-alkynylene, $R^1$, $R^2$ and $R^3$ are all methyl, R represents hydrogen, or $C_1$-$C_6$-alkyl, A represents the radical of the formula (A10)

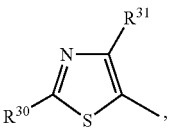 (A10)

in which $R^{30}$ represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 halogen atoms selected from the group consisting of fluorine, chlorine and bromine atoms, and $R^{31}$ represents fluorine, chlorine, bromine, hydroxyl, methyl, ethyl, methoxy, ethoxy, cyclopropyl, $C_1$-$C_2$-haloalkyl or $C_1$-$C_2$-haloalkoxy having 1 to 5 halogen atoms selected from the group consisting of fluorine, chlorine and bromine atoms.

3. The method of claim 1, wherein the compound of formula (I) is applied in admixture with one or more extenders, surfactants, or combinations thereof.

4. The method of claim 2, wherein the compound of formula (I) is applied in admixture with one or more extenders, surfactants, or combinations thereof.

* * * * *